United States Patent [19]
Goldstein et al.

[11] Patent Number: 5,298,431
[45] Date of Patent: Mar. 29, 1994

[54] PROCESS FOR PRODUCING LOW VISCOSITY ISOCYANATE TRIMERS

[75] Inventors: Stephen L. Goldstein; Edward A. Barsa, both of Cheshire, Conn.

[73] Assignee: Olin Corporation, Cheshire, Conn.

[21] Appl. No.: 767,946

[22] Filed: Sep. 30, 1991

[51] Int. Cl.⁵ .............................. C08F 6/00; C08F 6/10
[52] U.S. Cl. .................................... 528/491; 528/497; 528/502; 560/352
[58] Field of Search ...................... 528/491, 497, 502; 560/352

[56] References Cited

U.S. PATENT DOCUMENTS

| | | | |
|---|---|---|---|
| 4,220,728 | 9/1980 | Kresta et al. | 521/121 |
| 4,265,798 | 5/1981 | Mishra | 260/32.4 |
| 4,324,879 | 4/1982 | Bock et al. | 528/45 |
| 4,412,073 | 10/1983 | Robin | 544/193 |
| 4,876,380 | 10/1989 | Chen et al. | 560/352 |
| 4,963,675 | 10/1990 | Robin et al. | 544/222 |

Primary Examiner—John Kight, III
Assistant Examiner—Duc Troung
Attorney, Agent, or Firm—Dale L. Carlson

[57] ABSTRACT

This invention relates to a multi-step process for isolating a cyclotrimerized isocyanate from mixture containing said cyclotrimerized isocyanate plus an isocyanate oligomer which comprises the steps of: (a) contacting said mixture with a liquid solvent to provide a solvent-containing mixture, (b) extracting said solvent-containing mixture by liquid-liquid extraction to cause said solvent-containing mixture to elute into an extractate and a residue, wherein said extractate is a cyclotrimerized isocyanate that is essentially oligomer-free and is further characterized by having reduced viscosity relative to said solvent-containing mixture, and (c) separating uncyclotrimerized monomer from said extractate to provide a reduced viscosity trimer product that is essentially free of monomer. Also disclosed is the reduced-viscosity product produced by this process.

8 Claims, No Drawings

PROCESS FOR PRODUCING LOW VISCOSITY ISOCYANATE TRIMERS

FIELD OF THE INVENTION

This invention relates generally to isocyanurate adducts, and, more specifically, to a process for preparing low viscosity isocyanate trimers that are essentially free of high viscosity, high molecular weight oligomers and are preferably characterized as being clear and free of color.

BACKGROUND OF THE INVENTION

Polyisocyanurate adducts of polyisocyanates are well-known polyurethane intermediates used in the preparation of high performance urethane coatings, paints, and films. These adducts provide improved physical properties when used in such applications, as compared to dysfunctional isocyanates such as toluene diisocyanate. In addition, these adducts provide reduced volatility and an associated reduced toxicity hazard during use, as compared to toluene diisocyanate.

Processes for preparing these adducts are well known. Examples illustrative of these processes can be found in U.S. Pat. Nos. 4,220,728; 4,265,798; 4,324,879; and 4,412,073. Generally, the prior art processes involve adding a catalyst which promotes the isocyanate to isocyanurate (also known as "trimerization") reaction to the precursor isocyanate, optionally in the presence, but usually in the absence, of a solvent, allowing the reaction to proceed to the desired extent and then stopping the reaction with a suitable quenching reagent which destroys the activity of the catalyst. After the residual, unreacted precursor isocyanate is removed, the resulting material, in the case where the precursor isocyanate is a diisocyanate, is a mixture of oligomers composed of 3, 5, 7, etc. precursor diisocyanate molecules joined by 1, 2, 3, etc. isocyanurate rings. Usually, this mixture is simply called "trimer".

In the case where the precursor isocyanate is polyisocyanate, the reaction is stopped well before all the isocyanate groups have been converted to isocyanurate groups because, otherwise, the resulting product would be an unusable polymer having a very high (theoritically infinite) molecular weight and viscosity. However, the cost of equipment and energy to remove residual, unreacted precursor isocyanate dictate that the reaction not be stopped too soon. Generally, the reaction is run to more than 10% conversion but less than 50% conversion. The preferred range is between 25 and 35%. The resulting mixture of oligomers has a viscosity that is low enough to be suitable for some applications. However, for many uses, especially spray-coating and spray-painting applications, the viscosity of the product must be reduced with solvents. The use of solvents is often not desired because of their attendant hazards to workers and the environment. A preferred approach would be embodied in an adduct mixture of inherently lower viscosity, specifically, one containing a higher concentration of monomeric and low molecular weight oligomeric isocyanate adducts and a lower concentration of the high molecular weight oligomers.

A collateral problem in the trimerization reaction, namely the formation of color species in the product, can arise if the reactants, solvents and equipment are not scrupulously clean, pure and free of contaminants, especially oxygen. Since these conditions can not always be achieved, it would be desirable to have a method to treat the product so as to free the product from the color species. This would provide assurance that the trimer product would not impart an undesirable color to the final coating or film.

Methods for producing high purity polyisocyanates containing an isocyanurate moiety (so-called "isocyanurate polyisocyanates") are known in the art. By way of illustration, U.S. Pat. No. 4,963,675 discloses a process for extracting unreacted diisocyanate monomer and diisocyanate dimer, that is, the product formed from two molecules of diisocyanate monomer joined by an uretidione ring, from a cyclotrimerized diisocyanate by extracting the impure cyclotrimerized diisocyanate with an inert gas in either the liquid or supercritical state. Unfortunately, the elevated temperatures and pressures generally required to carry out the process of the '675 patent entail high equipment and operational costs which make this process less satisfactory a commercial standpoint than might be desired.

In addition, the product mixtures obtained from the process of the '675 patent will still contain any high molecular weight oligomers and any color bodies that may have been present in the starting material. As such, they will tend to have higher viscosity and/or a greater amount of discoloration (e.g., yellow color) than is desired for many applications. Unfortunately, no methods are currently known, to the knowledge of the current inventors, for separating these higher molecular weight oligomers from the desired, low molecular weight, "monomeric" trimer, that is, the product formed from three molecules of diisocyanate monomer joined by one isocyanurate ring. Accordingly, new methodology which provides polyisocyanurate adducts having a higher degree of purity and which are further characterized by reduced viscosity or a combination of reduced discoloration and reduced viscosity, relative to commercially available polyisocyanurate adducts, would be highly desired by the specialty isocyanates manufacturing community. Heretofore, adducts possessing such enhanced properties have not been known based upon the knowledge of the present inventors.

SUMMARY OF THE INVENTION

In one aspect, the present invention relates to a process for isolating a low molecular weight, low viscosity, "monomeric" cyclotrimerized isocyanate from a mixture containing said cyclotrimerized isocyanate plus high molecular weight, high viscosity, oligomeric polyisocyanurate polyisocyanates which comprises the steps of:

(a) contacting said mixture with a liquid solvent to provide a solvent-containing mixture, (b) extracting said solvent-containing mixture by liquid-liquid extraction to cause said solvent-containing mixture to elute into an extractate and a residue, wherein said extractate is a cyclotrimerized isocyanate that is essentially free of higher oligomers and is further characterized by having a reduced viscosity (preferably no greater than 700 centipoise) relative to said solvent-containing mixture, and (c) separating the solvent and any residual, unreacted monomer from said extractate to provide a reduced viscosity trimer product that is essentially free of solvent and unreacted monomer.

In another aspect, the present invention relates to the reduced viscosity trimer product produced by the above process.

These and other aspects will become apparent upon reading the following detailed description of the invention.

DETAILED DESCRIPTION OF THE INVENTION

In accordance with the present invention, the product stream produced in the trimerization of aliphatic diisocyanate(s) and containing higher molecular weight trimer oligomers is extracted in a suitable solvent to provide an extractate having reduced viscosity of less than about 750 centipoise and a higher viscosity residue. The extractate is suitable for use in high performance applications, and applications where a low viscosity trimer is needed, whereas the residue is suitably employed, preferably as a blend or admixture with conventional isocyanate product mixtures, in conventional aliphatic diisocyanate trimer applications.

The process of the present invention is suitably employed in the production of a wide range of isocyanate trimers, including hexamethylene diisocyanate ("HDI") trimer, isophorone diisocyanate ("IPDI") trimer, and $H_{12}$ MDI trimer, and the like.

The extraction of step (b) of the process of the present invention is carried out by conventional techniques which are well-known in the art. For example, background information on extraction is provided in Kirk-Othmer's "Encyclopedia of Chemical Technology", 3rd Ed., Wiley Interscience, 1980, Vol. 9, pp. 672–721. The product stream from the trimerization reaction and the eluting solvent are typically introduced at opposite ends of a packed extraction column (countercurrent extraction) or at the same end of the extraction column (cocurrent extraction). The solvent employed is suitably an organic solvent wherein the solvation power of the solvent favors solvation of the trimer and other monomeric species over the oligomeric isocyanurate compounds in the mixture to be eluted. Non-polar aliphatic and cycloaliphatic hydrocarbons are preferred as solvents.

The separation of step (c) of the process of the present invention is preferably carried out by evaporation of most of the solvent by any convenient means including simple distillation or thin film evaporation at elevated temperatures and atmospheric or reduced pressure, followed by a more stringent process for removal of any residual solvent and any unreacted diisocyanate monomer that was present in the starting material and which is concentrated in the extractate. This latter step is preferably accomplished using a wiped film evaporator ("WFE") in which the exposure of the product stream to high temperatures is minimized. The use of WFE is well-known in the art. Briefly, the process involves passing the monomer containing feed through the WFE apparatus at elevated temperatures, (preferably between about 80° C. and about 180° C., more preferably between 100° and 140° C.), and reduced pressure, (preferably between about 0.01 and about 5 mm Hg, more preferably between 0.1 and 2 mm Hg). The feed rate is dependant on the heated surface area of the apparatus, but should be slow enough to permit the removal of most of the residual diisocyanate monomer but fast enough to assure that the product is not exposed to high temperatures for an unnecessarily long period of time. At the end of this treatment, the residual monomer content should be less than 0.2%, preferably less than 0.1% by weight of the product.

A variety of solvents which do not react with isocyanates can be used in the process of the present invention under a variety of temperatures and pressures, including those conditions under which the solvent exists as a supercritical fluid. It is only necessary that a combination of solvent, pressure and temperature be found where the solvation power of the solvent favors the monomeric isocyanurate species over the oligomeric isocyanurate compounds in the mixture. Since the polarity of isocyanurates tend to increase with oligomerization (i.e., the greater the number of isocyanurate rings in the molecule, the higher will be its polarity), non-polar aliphatic and cycloaliphatic hydrocarbons and some ethers are preferred solvents. Low molecular weight, low boiling aliphatic and cycloaliphatic hydrocarbons such as pentane, hexane, heptane, cyclopentane, cyclohexane, methylcyclohexane and the like are the most preferred because of their selectivity and the ease with which they can be separated from the product isocyanurate.

A wide range of temperatures is suitably used in the process of this invention. One factor to be considered in the selection of preferred extraction temperatures is the balance of extraction rate with the degree to which the monomeric isocyanurate species are selectively separated from the oligomeric isocyanurate compounds in the mixture. Generally, somewhat elevated temperatures are preferred because more material is extracted per unit volume of solvent, however, very high temperatures should be avoided because of a loss in selectivity. Temperatures between 40° and 120° C. are preferred with temperatures between 50° and 90° C. being most preferred. A range of pressures may be used in the process of this invention. The factors to be considered in the selection of preferred extraction pressures are: the balance of extraction rate with the degree to which the monomeric isocyanurate species are selectively separated from the oligomeric isocyanurate compounds in the mixture; and, the added costs operating at supra-ambient pressures. Generally, somewhat elevated pressures are preferred because more material is extracted per unit volume of solvent, however, very high pressures should be avoided because of a loss in selectivity. Pressures between 1.0 and 2.1 atmospheres are preferred with pressures between 1.0 and 1.2 atmospheres being most preferred.

The following examples are intended to illustrate, but in no way limit the scope of, the present invention.

EXAMPLE 1

A sample of yellow colored 1,6-diisocyanatohexane (HDI) trimer was charged to a 1 L. liquid/liquid extraction apparatus and approximately 900 mls. hexane were added to fill the apparatus to the overflow arm. The overflow arm was fitted with solvent reservoir consisting of a 500 ml. flask containing approximately 300 mls. hexane and a magnetic stirrer. Heat was applied to this flask. After several hours of extraction, the hexane was removed from the contents of the reservoir under reduced pressure. The remaining material was nearly water white. Similarly, after the hexane had been stripped from the extractor contents, the residue was found to be more yellow than the starting material. The oligomer distribution of the starting material, extractate and residue, by GPC, were found to be:

| | OLIGOMER DISTRIBUTION (Wgt %) | | | |
|---|---|---|---|---|
| Sample Description | Trimer | Pentamer | Heptamer | Higher |
| Starting Material | 48.4 | 21.3 | 12.7 | 17.6 |
| Extractate | 95.5 | 4.5 | — | — |
| Residue | 39.0 | 24.8 | 15.1 | 21.2 |

EXAMPLE 2

A sample of HDI trimer was charged to a 1 L. liquid/liquid extraction apparatus and approximately 900 mls. cyclohexane were added to fill the apparatus to the overflow arm. The overflow arm was fitted with solvent reservoir consisting of a 500 ml. flask containing approximately 300 mls. cyclohexane and a magnetic stirrer. Heat was applied to this flask. After several hours of extraction, the cyclohexane was removed from the contents of the reservoir under reduced pressure. The remaining material was nearly water white. Similarly, the cyclohexane was stripped from the extractor contents. The oligomer distribution of the starting material, extractate and residue, by GPC, were found to be:

| | OLIGOMER DISTRIBUTION (Wgt %) | | | |
|---|---|---|---|---|
| Sample Description | Trimer | Pentamer | Heptamer | Higher |
| Starting Material | 71.4 | 20.5 | 7.7 | — |
| Extractate | 85.0 | 12.8 | 1.5 | — |
| Residue | 61.0 | 26.5 | 12.3 | — |

EXAMPLE 3

A sample of HDI trimer was charged to a 1 L. liquid/liquid extraction apparatus and approximately 900 mls. diisopropyl ether were added to fill the apparatus to the overflow arm. The overflow arm was fitted with solvent reservoir consisting of a 500 ml. flask containing approximately 300 mls. diisopropyl ether and a magnetic stirrer. Heat was applied to this flask. After several hours of extraction, the diisopropyl ether was removed from the contents of the reservoir under reduced pressure. The remaining material was very slightly colored. Similarly, the diisopropyl ether was stripped from the extractor contents. The oligomer distribution of the starting material, extractate and residue, by GPC, were found to be:

| | OLIGOMER DISTRIBUTION (Wgt %) | | | |
|---|---|---|---|---|
| Sample Description | Trimer | Pentamer | Heptamer | Higher |
| Starting Material | 59.8 | 21.0 | 9.9 | 9.3 |
| Extractate | 79.6 | 17.5 | 2.9 | — |
| Residue | 44.4 | 24.5 | 15.6 | 15.4 |

EXAMPLE 4

About 653 grams of pale yellow (APHA color was approximately 75) HDI trimer was charged to a 2 L. liquid/liquid extraction apparatus and approximately 1400 mls. cyclohexane were added to fill the apparatus to the overflow arm. The overflow arm was fitted with solvent reservoir consisting of a 1000 ml. flask containing approximately 700 mls. cyclohexane and magnetic stirrer. Heat was applied to this flask. The extraction was allowed to proceed until approximately 60% of the trimer had been extracted into the reservoir. After removal of the solvent from the contents of the extractor, 260 grams of darker yellow, viscous liquid was isolated—the "heavy" fraction. Similarly, the cyclohexane was removed from the contents of the reservoir under reduced pressure to yield 392 grams of a mobile, water white liquid. This material was charged to the extractor and subjected to further extraction as described above. The extraction was allowed to proceed until approximately 50% of the trimer had been extracted into the reservoir. After removal of the solvent from the contents of the extractor, 142 grams of an essentially colorless, mobile liquid was isolated—the "medium" fraction. Similarly, the cyclohexane was removed from the contents of the reservoir under reduced pressure to yield 161 grams of a very mobile, water white liquid—the "light" fraction. The oligomer distribution and the viscosities of the starting material and the three fractions are shown in Table 1 below.

EXAMPLE 5

About 464 grams of light yellow (APHA color was approximately 125) HDI trimer was charged to a 1 L. liquid/liquid extraction apparatus and approximately 600 mls. cyclohexane were added to fill the apparatus to the overflow arm. The overflow arm was fitted with solvent reservoir consisting of a 500 ml. flask containing approximately 400 mls. cyclohexane and magnetic stirrer. Heat was applied to this flask. The extraction was allowed to proceed until approximately 60% of the trimer had been extracted into the reservoir. After removal of the solvent from the contents of the reservoir, 289 grams of colorless, mobile liquid was isolated—the "light" fraction. The reservoir flask was partially filled with cyclohexane and the extraction was continued until about 60% of the remaining trimer had been extracted into the reservoir. After removal of the solvent from the contents of the extractor 73 grams of viscous very slightly yellow liquid was isolated—the "heavy" fraction. The residual trimer remaining in the extractor was yellow to brown, very viscous fluid. The oligomer distribution and the viscosities of the two fractions are shown in Table 2 below.

EXAMPLE 6

About 206 grams of the "light" fraction of Example 5 was charged to a 1 L. liquid/liquid extraction apparatus and extracted with cyclohexane as described in Example 5 above. The extraction was allowed to proceed until approximately 60% of the trimer had been extracted into the reservoir. After removal of the solvent from the contents of the reservoir, 105 grams of a colorless, mobile liquid was isolated—the "light" fraction. After removal of the solvent from the contents of the extractor, 78 grams of less mobile, colorless liquid was isolated—the "heavy" fraction. The oligomer distribution and the viscosities of the starting material and the two fractions are shown in Table 3 below.

TABLE 1

HDI TRIMER/CYCLOHEXANE EXTRACTION
EXAMPLE 4 RESULTS

| | OLIGOMER DISTRIBUTION (Wgt %) | | | | |
|---|---|---|---|---|---|
| Sample Description | Trimer | Pentamer | Heptamer | Higher | Viscosity cps, 25° C. |
| Starting Material | 50.8 | 22.0 | 13.5 | 13.6 | 3,400 |
| Light Fraction | 89.2 | 8.1 | 2.7 | — | 610 |
| Medium Fraction | 58.8 | 27.1 | 14.1 | — | 1,425 |

TABLE 1-continued

HDI TRIMER/CYCLOHEXANE EXTRACTION
EXAMPLE 4 RESULTS

| Sample Description | Trimer | OLIGOMER DISTRIBUTION (Wgt %) | | | Viscosity cps, 25° C. |
|---|---|---|---|---|---|
| | | Pent-amer | Hept-amer | Higher | |
| Heavy Fraction | 10.8 | 29.9 | 27.4 | 31.9 | 46,300 |

TABLE 2

HDI TRIMER/CYCLOHEXANE EXTRACTION
EXAMPLE 5 RESULTS

| Sample Description | Trimer | OLIGOMER DISTRIBUTION (Wgt %) | | | Viscosity cps, 25° C. |
|---|---|---|---|---|---|
| | | Pent-amer | Hept-amer | Higher | |
| Light Fraction | 76.3 | 19.5 | 3.6 | 0.6 | 1,180 |
| Heavy Fraction | 21.6 | 37.8 | 26.6 | 13.9 | 11,600 |

TABLE 3

HDI TRIMER/CYCLOHEXANE EXTRACTION
EXAMPLE 6 RESULTS

| Sample Description | Trimer | OLIGOMER DISTRIBUTION (Wgt %) | | | Viscosity cps, 25° C. |
|---|---|---|---|---|---|
| | | Pent-amer | Hept-amer | Higher | |
| Starting Material | 76.3 | 19.5 | 3.6 | 0.6 | 1,180 |
| Light Fraction | 92.8 | 7.2 | — | — | 580 |
| Heavy Fraction | 52.3 | 36.5 | 9.0 | 2.2 | 2,500 |

While the invention has been described above with references to specific embodiments thereof, it is apparent that many changes, modifications and variations in the materials, arrangements of parts and steps can be made without departing from the inventive concept disclosed herein. For example, in employing the of the present invention, Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

Having thus described the invention, what is claimed is:

1. A process for isolating a low molecular weight, low viscosity, "monomeric" cyclotrimerized isocyanate selected from the group consisting of hexamethylene diisocyanate trimer, isophorone diisocyanate trimer, and combinations thereof, from a mixture containing said cyclotrimerized isocyanate plus high molecular weight, high viscosity, oligomeric polyisocyanurate polyisocyanates which comprises the steps of:
   (a) contacting said mixture with a liquid solvent selected from the group consisting of pentane, hexane, heptane, cyclopentane, cyclohexane, methylcyclohexane, and combinations thereof, to provide a solvent-containing mixture,
   (b) extracting said solvent-containing mixture by liquid-liquid extraction to cause said solvent-containing mixture to elute into an extractate and a residue, wherein said extractate is a cyclotrimerized isocyanate selected from the group consisting of pentane, hexane, heptaine, cyclopentane, cyclohexane, methylcyclohexane, and combinations thereof, that is essentially free of higher oligomers and is further characterized by having a reduced viscosity relative to said solvent-containing mixture, and
   (c) separating the solvent and any residual, unreacted monomer from said extractate, using a wiped film evaporator at an elevated temperature of between 80 and 180 degrees Centegrade, to provide a reduced viscosity trimer product that is essentially free of solvent and unreacted monomer.

2. The process of claim 1 wherein said extractate has a viscosity of no greater than 700 centipoise.

3. The process of claim 1 wherein the weight percent of solvent in said solvent-containing mixture is between about 1 and about 25.

4. The process of claim 1 wherein the step (c) separating is carried out using evaporation.

5. The process of claim 4 wherein said evaporation is effected by means of a wiped film evaporator.

6. The extractate produced by the process of step (b) of claim 1 which has an oligomer content of no greater than about seven percent based upon the total weight of the extractate.

7. The extractate produced by the process of step (b) of claim 1 which contains at least 88 weight percent of isocyanate trimer based upon the total weight of the extractate.

8. The reduced viscosity trimer product produced by the process of claim 1.

* * * * *